United States Patent [19]

Chao et al.

[11] Patent Number: 4,544,781
[45] Date of Patent: Oct. 1, 1985

[54] CONTROL OF TEMPERATURE EXOTHERMS IN THE CONVERSION OF METHANOL TO GASOLINE HYDROCARBONS

[75] Inventors: Paul K. Chao, Philadelphia, Pa.; Kevin J. Knob, Pitman, N.J.; Sergei Yurchak, Media, Pa.

[73] Assignee: Mobil Oil Corporation, New York, N.Y.

[21] Appl. No.: 690,078

[22] Filed: Jan. 9, 1985

[51] Int. Cl.⁴ .............................................. C07C 1/20
[52] U.S. Cl. ............................ 585/408; 208/DIG. 1; 422/105; 422/110; 422/194; 422/198; 422/207; 422/211; 585/401; 585/469; 585/640; 585/501; 585/733
[58] Field of Search ................. 208/DIG. 1; 422/194, 422/206, 198, 207, 211, 190, 191, 105, 110; 585/408, 401, 402, 403, 469, 640, 501, 701, 733

[56] References Cited

U.S. PATENT DOCUMENTS

| | | | |
|---|---|---|---|
| 2,884,372 | 4/1959 | Bergstrom | 422/211 |
| 2,980,515 | 4/1961 | Horner et al. | 422/211 |
| 3,894,105 | 7/1975 | Chang et al. | 260/668 R |
| 3,894,107 | 7/1975 | Butter et al. | 260/668 R |
| 3,962,127 | 6/1976 | Woerner | 252/419 |
| 4,012,335 | 3/1977 | Woerner | 252/419 |
| 4,041,099 | 8/1977 | Hutson, Jr. | 422/211 |
| 4,076,761 | 2/1978 | Chang et al. | 260/668 R |
| 4,482,772 | 11/1984 | Tabak | 585/254 |
| 4,506,106 | 3/1985 | Hsia et al. | 585/312 |

Primary Examiner—D. E. Gantz
Assistant Examiner—A. Pal
Attorney, Agent, or Firm—Alexander J. McKillop; Michael G. Gilman; Van D. Harrison, Jr.

[57] ABSTRACT

A reactor bed, particularly one designed for converting alcohols to gasoline, is provided with a section downstream of the catalyst bed filled with high heat capacity thermal absorptive material. When the circulation of recycled gas to the system is temporarily suspended automatic valves terminate the injection of alcohol feedstock and begin the injection of inert gases such as methane into the system, thereby avoiding the formation of a hot spot which would subsequently damage the catalyst and equipment downstream.

17 Claims, 5 Drawing Figures

4,544,781

CONTROL OF TEMPERATURE EXOTHERMS IN THE CONVERSION OF METHANOL TO GASOLINE HYDROCARBONS

NATURE OF THE INVENTION

This invention is concerned in general with the production of gasoline boiling-range hydrocarbons by flowing an alcohol or ether starting material such as methanol, dimethyl ether or mixtures containing such, through a catalyst bed. More particularly the present invention is concerned with a process and apparatus for controlling the localized temperature increases that occur within the catalyst bed when operating conditions, notably the recirculation of gas, are interrupted.

PRIOR ART

The catalytic conversion of methanol and dimethyl ether to gasoline is a well known process in the prior art for manufacturing hydrocarbon fuels useful as gasoline fuels. For example, U.S. Pat. No. 3,894,107 discloses the conversion of alcohols to aromatic hydrocarbons by contacting the alcohol with a zeolite catalyst having a silica to alumina ratio of at least about 12 and a Constraint Index of about 1 to 12 at suitable temperature and pressure conditions. Useful zeolites are exemplified by ZSM-5, ZSM-11, ZSM-12 and ZSM-21.

U.S. Pat. No. 3,894,105 discloses the conversion of methanol and dimethyl ether to aromatic mixtures rich in tetramethyl benzene isomers, particularly durene utilizing zeolite catalysts.

U.S. Pat. No. 4,012,335 describes a catalyst bed which has positioned at either end of it a mass of ceramic spheres or balls which serve as a heat sink for the process conducted within the bed. U.S. Pat. Nos. 3,894,107; 3,894,105; and 4,012,335 are incorporated herein by reference.

The catalytic conversion of methanol to gasoline is an exothermic reaction which within the catalyst bed generates about 650 BTU per pound of methanol and dimethylether expressed as methanol in the catalyst bed. This heat normally is released under controlled conditions which are achieved by the recycle of light hydrocarbon gases over the catalyst bed. With the recycle of gas it is possible to limit the temperature increase to about 100° F. thereby restraining the maximum temperature to less than 800° F. As long as there is sufficient recycle gas, excessive temperature is not a problem. However, there may occur instances when the circulation of recycled gas is interrupted or suspended, but the methanol feedstock continues to flow through the catalyst bed, and react to release heat. Localized temperatures reach as high as 1400° F. rapidly with consequent damage to the catalyst. Increased temperature accelerates the rate of reaction. When such a temperature increase occurs the methanol flow must be stopped to avoid excessive damage to the catalyst and the "hot spot" generated in the catalyst bed must be dissipated in such a way that the high temperature will not damage the catalyst or downstream equipment. Ordinarily the temperature increase is very rapid and the zone wherein this increase occurs is relatively narrow in width. Thermocouples attached along the longitudinal axis of the catalyst bed will not be able to detect the excess temperature fast enough to prevent a runaway situation with ensuing damage to the catalyst. A control system activated by detecting a loss of recycle gas flow would provide the necessary rapid detection.

SUMMARY OF THE INVENTION

Briefly stated, this invention comprises a process and apparatus wherein upon the cessation of flow of recycled gas to the catalyst reactor bed in a methanol-to-gasoline reactor, the injection of a non-reactive purge gas, such as a natural gas is begun immediately at the point of injection of methanol. A mass of high thermal capacity spheres such as ceramic balls is placed at the downstream end of the catalyst bed so that as the high-temperature thermal front progresses through the catalyst bed it contacts the high thermal capacity material where it is dissipated. It is further dissipated by additional injection of the inert purge gas.

DESCRIPTION OF THE INVENTION

Figure 1:
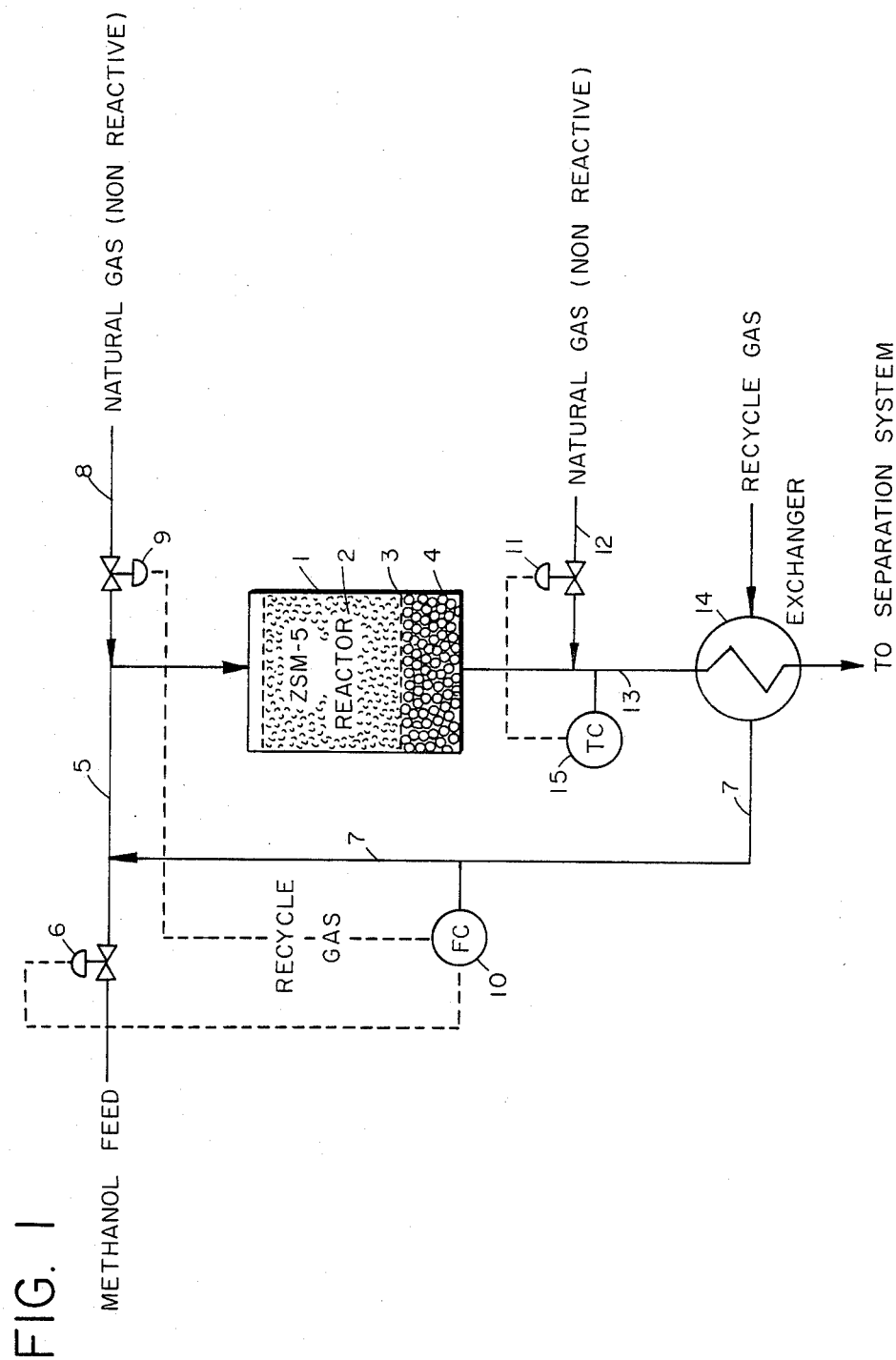
FIG. 1 is a flow sheet depicting the process and apparatus of this invention.

This invention, it is believed, can best be understood by reference to FIG. 1 which is a flowsheet for a preferred embodiment of the invention. In FIG. 1 reference number 1 indicates generally a reactor bed containing a catalyst capable of converting methanol and/or methyl ether to aromatic hydrocarbons, some boiling within the range of gasoline. Reactor 1 contains within it the catalyst section 2 which can comprise a catalyst such as zeolite ZSM-5 or the like. Other catalysts are disclosed in U.S. Pat. Nos. 3,894,105 and 3,894,107. Reference numeral 3 denotes a perforated screen supporting the catalyst bed proper above a lower section 4 filled with spheres or balls made up of some heat absorbent material such as a ceramic material. Line 5 carries the heated vaporized methanol feedstock into the reactor bed 2, its flow being controlled by valve 6. Because the reaction converting methanol to aromatic hydrocarbons is an exothermic one, recycle gas is continually circulated into line 5 through line 7 to maintain the temperature in the reactor bed within a desired range between 600° and 850° F. The recycle gas ordinarily is obtained as part of the overhead gas in separating the reactor product effluent downstream. Flow sensor and flow control device 10 controls the flow of methanol feedstock through valve 6, as well as the flow of natural gas (or other nonreactive gas) through conduit 8 and valve 9 and optionally through valve 11 in conduit 12. Line 13 carries effluent from reactor 1, as well as any natural gas admitted through valve 11. Heat exchanger 14 supplies some heat to the recycled gas being conducted back into the reactor since the reaction does require also a minimum temperature to sustain it.

Under normal operating conditions methanol or other types of feedstock flows through open valve 6 and line 5 and through catalyst bed 2 where it is converted with the release of heat into aromatic compounds which flow from the reactor bed 2, through section 4 filled with ceramic balls or other heat sorptive material and subsequently through line 13 for further processing in the system. In the event that it becomes necessary to close the recycle gas line 7 or, if recycle gas becomes unavailable, a zone of intense temperature within the catalyst bed 2 will be created of sufficient intensity as to seriously damage the catalyst contained within the reactor.

It is at this point that our invention comes into operation. Upon the loss of recycle gas flow through line 7 the control valve 10, which is appropriately designed to do so, senses the large flow decrease, immediately closes valve 6 shutting off the methanol feed and opens valve 9, thereby permitting the inflow of natural or non-reactive gas at a much cooler temperature. The natural or non-reactive gas flowing through the catalyst bed will displace ahead of it the gases and vapors in the high temperature zone and push them into the zone filled with the large size heat sorptive spheres or balls. It is particularly important that the steam present in the catalyst bed be displaced, inasmuch as prolonged exposure to water vapor at elevated temperatures reduces the catalyst's effectiveness. This material being at a much lower temperature will absorb a substantial quantity of the excess heat present in the displaced gases and vapors and will thus prevent any serious increase in temperature downstream and consequential damage to catalyst and equipment. The term "natural or non-reactive gas" is intended to include any gas which will provide a cooling function in the reaction zone and which will not react to generate heat. The gas thus can be any available gas such as natural gas comprising methane primarily or a gas such as nitrogen.

The ceramic balls, spheres or other heat sorptive material used herein can be made of any material which has a high heat capacity. Preferably the materials are alumina, silica, quartz or other refractory material.

When all danger from the temperature build-up has been eliminated the system can be put back on stream after the resumption of gas flow through line 7 by the gradual opening of valve 6. Valve 8 will be closed.

As an optional feature our invention also provides for the injection of a cooling gas at a point downstream of the reactor bed. This is shown as valve 11 in the drawing. Valve 11 can be controlled by temperature controller 15. This additional gas mixes with the displaced hot gases and dilutes them to a temperature where downstream equipment will not be damaged. Such gases are admitted through conduit 12 and valve 11, the latter also controlled by controller 15.

While we have described that the invention as applicable to a one-bed type reactor, it will be readily apparent to those skilled in the art that a similar type process and apparatus can be utilized with a 2-bed reactor for making gasoline fuels from methanol and dimethyl ether wherein the first bed comprises a dehydrating catalyst such as alumina and the effluent therefrom is conducted into a second bed comprising the ZSM-5 catalyst described before. In such a system the second bed can comprise a bed of catalyst having near its exit end a reactor filled with the heat absorptive material. There are also other processes wherein synthesis gas, i.e. a gas comprising primarily carbon monoxide and hydrogen, is first passed through a Fischer-Tropsch reactor and subsequently through a catalyst bed of zeolite catalyst to form aromatic hydrocarbons having a gasoline boiling point range and useful as motor fuels. The invention can be applied to beds of zeolite such as ZSM-5 in parallel with dehydration beds, zeolite beds in a series, in other parallel configurations, or other combinations.

EXAMPLE

Figure 2:
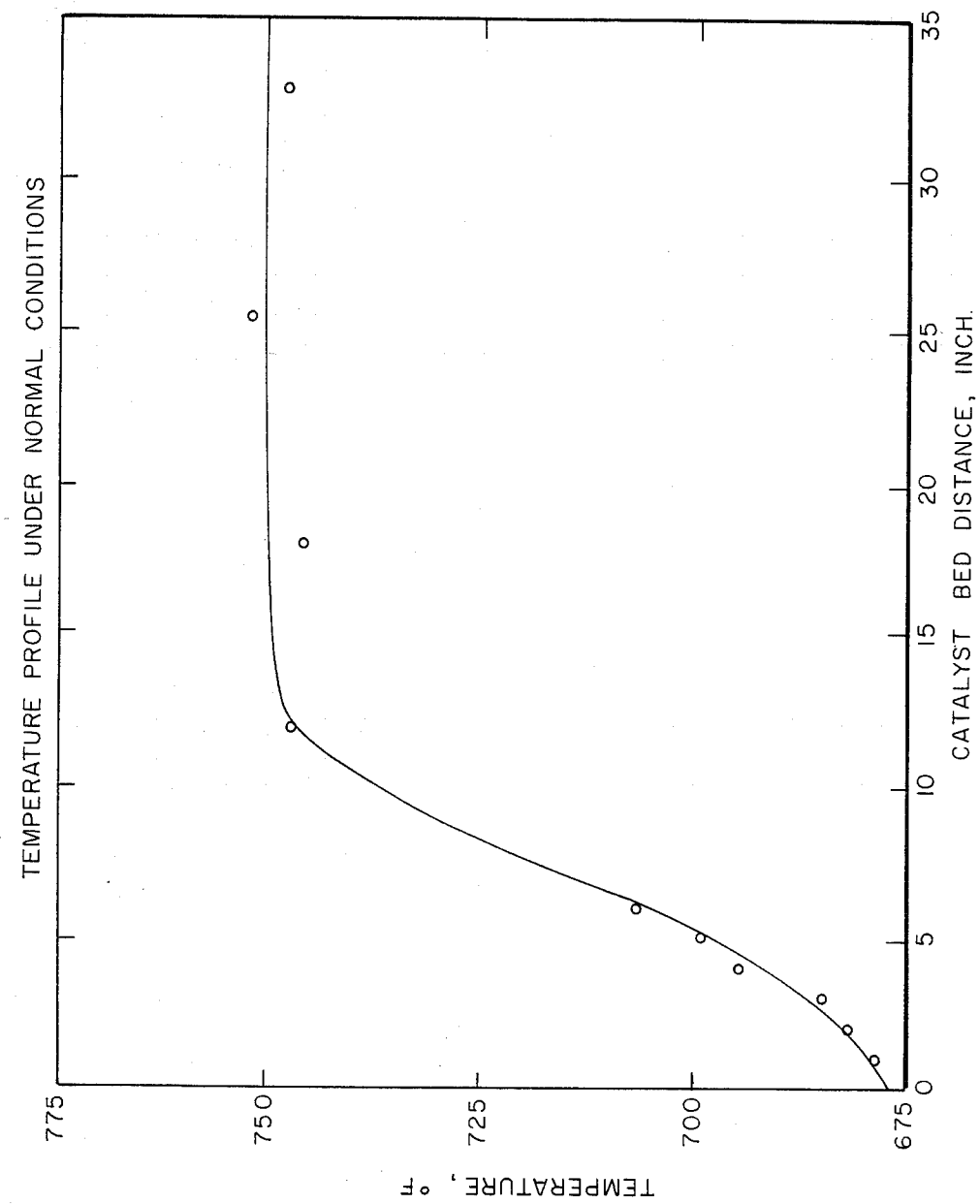
FIG. 2 is a longitudinal temperature profile of the catalyst bed operating under minimal conditions with an undisturbed recycling of recycle gas.
Figure 3:
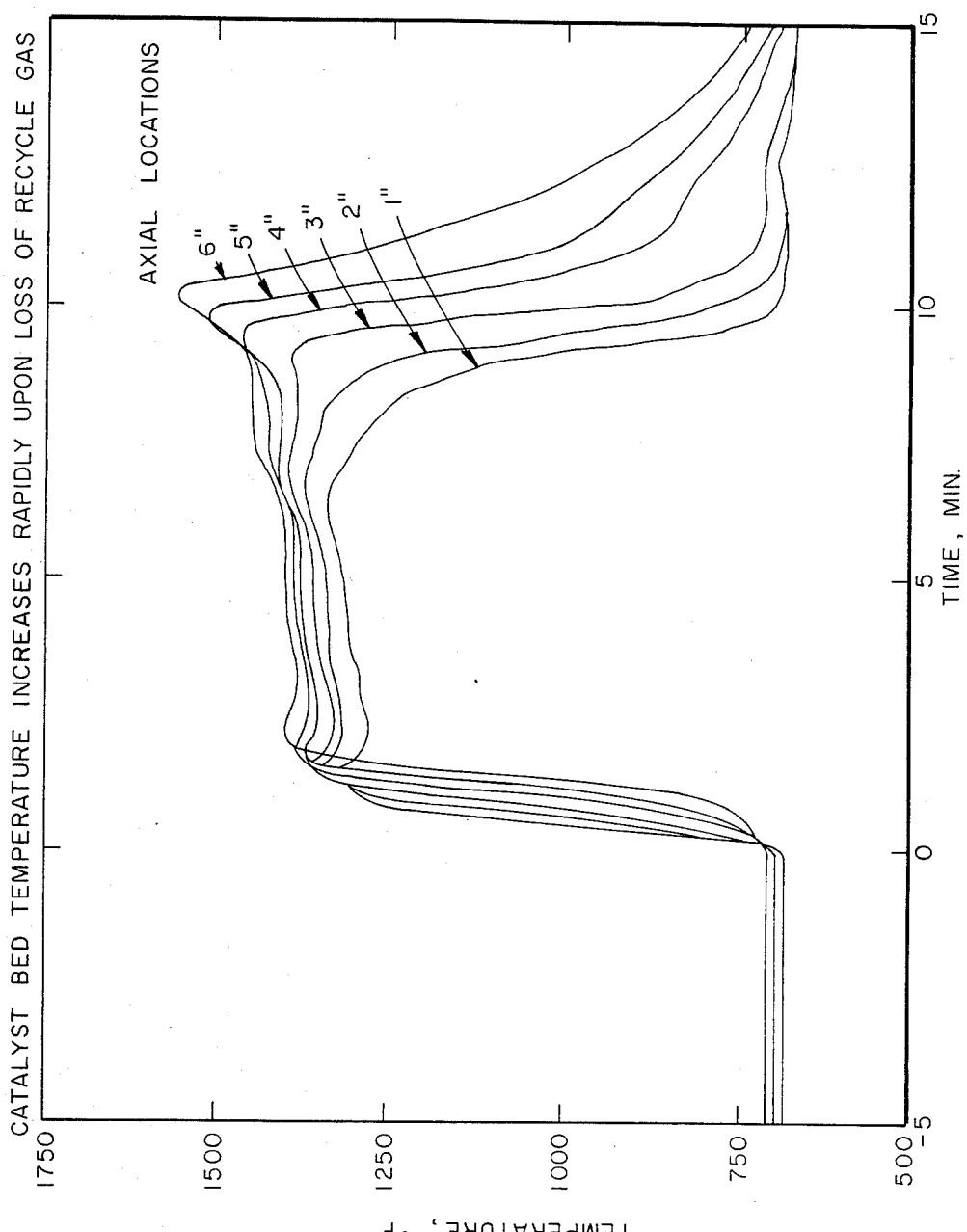
FIG. 3 is a graphical representation of the temperature fluctuation as a function of time at several locations or points in the catalyst bed after the recycling of recycle gas has been suspended.
Figure 4:
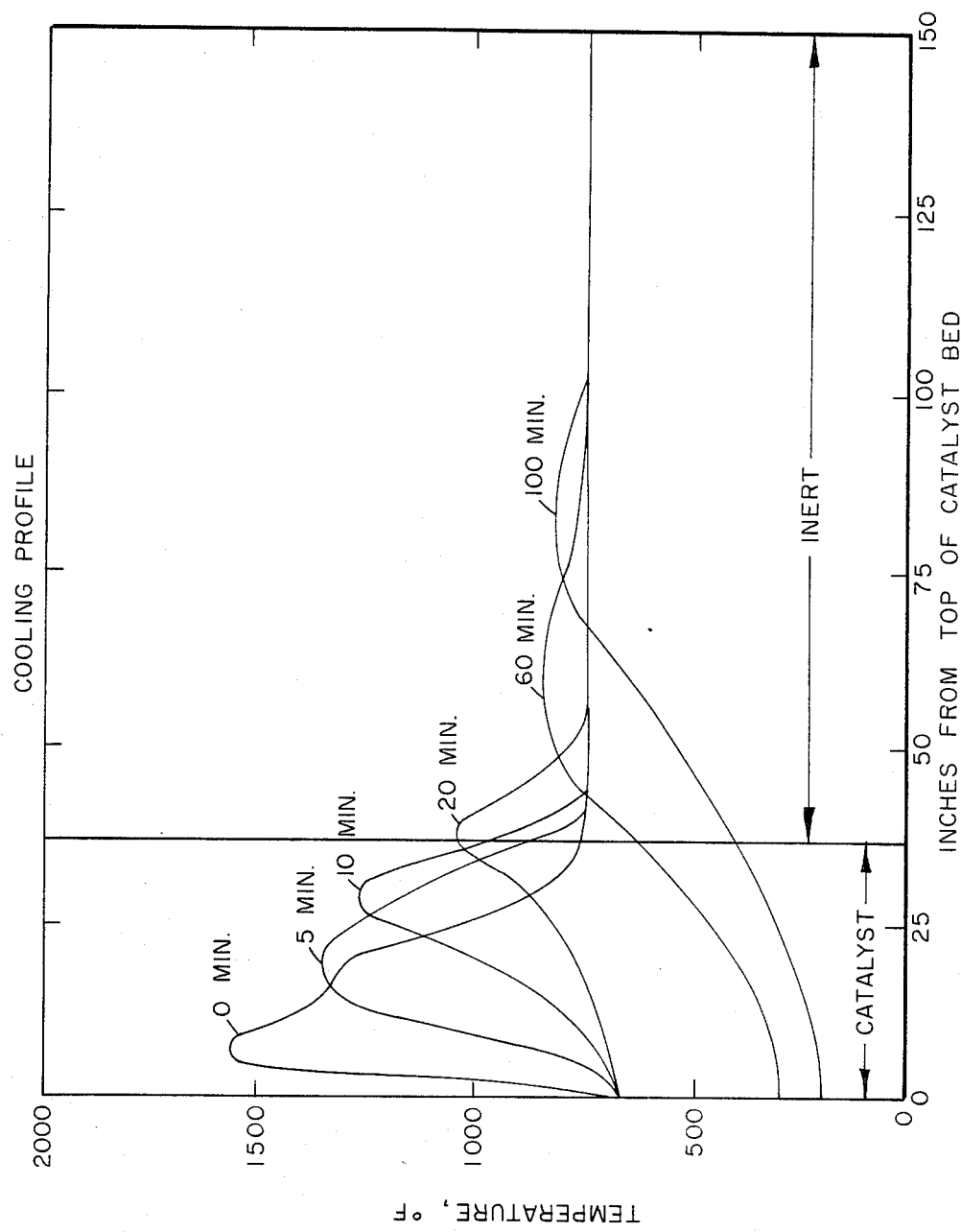
FIG. 4 is a series of longitudinal temperature profiles in the catalyst bed and inert bed after the injection of a purge gas.

A pilot unit having a design similar to that of FIG. 1 and capable of converting four barrels per day of methanol to gasoline was operated using a ZSM-5 catalyst at the conditions shown in Table 1 for approximately one day. The reactor section consisted of a three foot catalyst bed which was immediately followed by a section of six foot containing inert ceramic balls having the properties shown in Table 2. The temperature profile of the column shown in FIG. 2 was determined just before interrupting the recycle of gas flow. The profile was determined by measurements with thermocouples placed longitudinally along the axis of the catalyst bed. The flow of recycle gas through the catalyst bed was then stopped but the flow of methanol was continued. Upon this termination the temperature peak in the catalyst bed increased rapidly as shown in FIG. 3. Within approximately two minutes a portion of the catalyst bed attained a temperature of about 1400° F. After six minutes at such a temperature catalyst deactivation will begin. The deactivated catalyst also was responsible for increasing the methanol feed temperature to a point which resulted in a catalyst bed temperature exceeding 1400° F. FIG. 3 shows the progress of this zone of high temperature through the length of the catalyst bed over a period of approximately ten minutes. At the end of the ten minute period the injection of methane gas was begun into the reactor at a point corresponding to conduit 9 in FIG. 1 at a rate of 154 pounds per hour per square foot to remove the temperature peak. The resulting cooling profile is shown in FIG. 4. This profile shows that the hot spot dispersed and was reduced in magnitude as it passed through the catalyst and the section containing the ¾" diameter inert balls.

Figure 5:
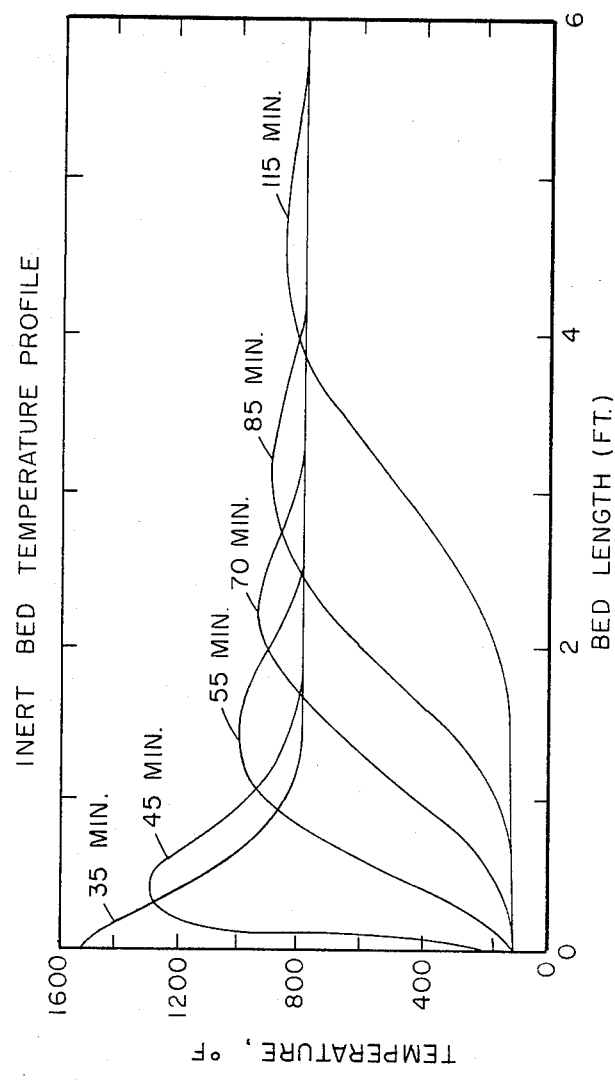
FIG. 5 is a calculated temperature profile of the inert section of the catalyst bed after the application of our invention.

The cooling profiles shown in FIG. 4 indicate that the hot spot can be reduced greatly in magnitude by placing a section of heat sorptive material downstream and by injecting a cooler non-reactive gas. FIG. 4 shows that the catalyst bed temperature decreases in magnitude as purge gas flows through the catalyst bed. This is because of heat loss from the small diameter reactor used (4"). A commercial size reactor would have much less heat loss. The effectiveness of the inert balls in reducing high temperature in FIG. 5 for an adiabatic system was determined using heat transfer coefficients calculated from the inert cooling profile data in FIG. 4.

As to the size of the section containing the heat sorptive material it will range to between 0.1 and 1 times the bulk volume of the reactor bed. This, of course, depends in part upon the heat sorption characteristics of the material.

TABLE 1

| | |
|---|---|
| Charge, pounds methanol/pounds water | 83/17 w/w methanol/water |
| Charge Rate* | 547 lb/hr-ft$^2$ |
| Methanol WHSV (Conv. Rx)* | 1.6 |
| Recycle Ratio | 9/1 |
| Pressure | 300 psig |
| Conv. Rx Inlet Temperature | 680° F. |

TABLE 1-continued

| | |
|---|---|
| Conv. Rx Outlet Temperature | 760° F. |
| Dehydration Rx Inlet Temperature | 600° F. |
| Dehydration Rx Outlet Temperature | 755° F. |

*Charge rate and methanol space velocity the same as if an 8-foot ZSM-5 catalyst bed were used. For recycle-gas-loss study, the length of the ZSM-5 catalyst bed was reduced to study the effect of the purge gas and inert balls because of reactor lengthlimitations.

TABLE 2

| Properties of Inert Alumina Ball | |
|---|---|
| Size | $\frac{3}{4}$" Sphere |
| Solid Density | 247 lb/ft$^3$ |
| Specific Heat | 0.283 BTU/Lb °F. |
| Thermal Conductivity | 1.8 BTU/Lb °F. - Ft. |

We claim:

1. In a process wherein an oxygenated hydrocarbon feedstock is contacted with a catalyst in a catalyst bed at a stabilized operating temperature, and thereby converted into a mixture containing hydrocarbons boiling within the boiling point range of gasoline, and a gaseous fraction obtained from the effluent from said reactor bed is reinjected into the process at a location upstream of said catalyst bed, the improvement comprising:
   (a) providing a source of a non-reactive gas which will provide a cooling effect at a temperature less than the stabilized operating temperature of said reactor bed;
   (b) providing a zone of heat absorptive material downstream of said catalyst bed at a temperature equal to or less than the stabilized operating temperature of said catalyst bed;
   (c) upon loss of flow of said gaseous fraction, flowing said non-reactive gas of (a) through said catalyst bed and through said zone of heat absorptive material; and
   (d) upon resumption of flow of said gaseous fraction through said catalyst bed, terminating the flow of said non-reactive gas and resuming the conversion of oxygenated hydrocarbon product to a mixture containing hydrocarbons boiling within the boiling point range of gasoline.

2. The process of claim 1 wherein the non-reactive gas of (c) is methane.

3. The process of claim 1 wherein the heat absorptive material is alumina.

4. The process of claim 1 wherein the heat absorptive material is silica.

5. The process of claim 1 wherein the heat absorptive material is quartz.

6. The process of claim 1 wherein the heat absorptive material is made up of spheres having an average diameter of between about $\frac{1}{4}$ inch and about 1 inch.

7. The process of claim 1 wherein said oxygenated hydrocarbon feedstock is methanol.

8. The process of claim 1 wherein said oxygenated hydrocarbon feedstock is dimethyl ether.

9. The process of claim 1 wherein said oxygenated hydrocarbon feedstock is derived from synthesis gas.

10. The process of claim 1 wherein said hydrocarbon feedstock is derived by contacting methanol with a dehydrating agent.

11. The process of claim 1 wherein the flow decrease of said non-reactive gas through said catalyst bed is initiated by a flow decrease in a conduit supplying the gaseous fraction.

12. Apparatus for converting an oxygenated hydrocarbon feedstock to a mixture containing hydrocarbons boiling within the boiling point range of gasoline comprising:
   (a) a source of said oxygenated hydrocarbons;
   (b) a catalyst bed containing a particulate catalyst suitable for converting said feedstock to gasoline hydrocarbons and having an upstream end and a downstream end;
   (c) a heat sorption zone containing a heat absorptive material having an upstream end and a downstream end;
   (d) a source of a relatively non-reactive gas which will provide a cooling effect and has a temperature equal to or less than the temperature in said catalyst bed;
   (e) means for separating effluent from said heat sorptive zone into liquid and gas phases;
   (f) conduit and valve means interconnecting said source of (a) to the upstream end of said catalyst bed; said downstream end of said catalyst bed to the upstream end of said heat sorptive zone; and said downstream end to said heat sorptive zone to said means for separating effluent; and
   (g) means for detecting failure of a supply of recycle gas to the catalyst and for injecting said non-reactive gas into said catalyst bed.

13. The apparatus of claim 12 and a second source of non-reactive gas having a temperature equal to or less than the temperature in said catalyst bed and connected by valve and conduit means into the effluent stream at a point downstream of said heat sorption zone.

14. The apparatus of claim 12 wherein said catalyst bed comprises a zeolite.

15. The apparatus of claim 12 wherein said catalyst bed comprises ZSM-5 zeolite.

16. The apparatus of claim 12 wherein said heat absorptive material is selected from the group consisting of alumina, silica and quartz.

17. The apparatus of claim 12 wherein said heat absorptive material comprises spheres having an average diameter between about $\frac{1}{4}$ inch and about 1 inch in diameter.

* * * * *